United States Patent
Leeper et al.

(10) Patent No.: US 12,091,456 B2
(45) Date of Patent: *Sep. 17, 2024

(54) TARGETING ANEURYSM DISEASE BY MODULATING PHAGOCYTOSIS PATHWAYS

(71) Applicant: The Board of Trustees of the Leland Stanford Junior University, Stanford, CA (US)

(72) Inventors: Nicholas J. Leeper, Stanford, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1030 days.

This patent is subject to a terminal disclaimer.

(21) Appl. No.: 17/029,814

(22) Filed: Sep. 23, 2020

(65) Prior Publication Data

US 2021/0095025 A1    Apr. 1, 2021

Related U.S. Application Data

(63) Continuation of application No. 15/510,591, filed as application No. PCT/US2015/049150 on Sep. 9, 2015, now Pat. No. 10,822,411.

(60) Provisional application No. 62/050,664, filed on Sep. 15, 2014.

(51) Int. Cl.
| | | |
|---|---|---|
| C07K 16/28 | (2006.01) | |
| A61K 38/17 | (2006.01) | |
| A61K 39/00 | (2006.01) | |
| A61P 9/10 | (2006.01) | |
| C12Q 1/6883 | (2018.01) | |

(52) U.S. Cl.
CPC .......... *C07K 16/2803* (2013.01); *A61K 38/17* (2013.01); *A61P 9/10* (2018.01); *C12Q 1/6883* (2013.01); *A61K 2039/505* (2013.01); *C07K 2317/24* (2013.01); *C07K 2317/76* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,492,096 B2 | 7/2013 | Pasche |
| 2008/0267909 A1 | 10/2008 | Tabas |
| 2012/0269731 A1 | 10/2012 | Wellstein et al. |

FOREIGN PATENT DOCUMENTS

| | | |
|---|---|---|
| WO | WO1996/36643 | 5/1996 |
| WO | WO2013/109752 | 7/2013 |
| WO | WO2015/041987 | 3/2015 |

OTHER PUBLICATIONS

Weiskipf, 2013, Science, vol. 341: 1-13 Whisstock et al., 2003, Quart. Rev. Bioph. vol. 3: 307-340.*

(Continued)

*Primary Examiner* — Amy E Juedes
(74) *Attorney, Agent, or Firm* — Pamela J. Sherwood; Bozicevic, Field & Francis LLP

(57) ABSTRACT

In the methods of the invention, an agent that increases phagocytosis and/or efferocytosis of cellular components of coronary plaque is administered to the subject in a dose and for a period of time effective to stabilize, prevent or reduce aneurysm disease in the individual.

7 Claims, 4 Drawing Sheets

Specification includes a Sequence Listing.

(56) References Cited

OTHER PUBLICATIONS

Cochran, 2000, Chem. Biol. vol. 7: R85-R94.*
Hruby, 2002, Nat. Rev. vol. 1: 847-858.*
Hatherley, 2007, J. Biol. Chem. vol. 282: 14567-14575.*
GenBank AAH33092.1 SIRPA protein, 2006, pp. 1-5.*
Leeper et al.(2013), "Loss of CDKN2B Promotes p53-Dependent Smooth Muscle Cell Apoptosis and Aneurysm Formation" vol. 33, No. 1, pp. e1-e10, Arteriosclerosis, Thrombosis, and Vascular Biology.
Kojima et al., (2014) "Cyclin-dependent kinase inhibitor 2B regulates efferocytosis and atherosclerosis" vol. 124, No. 3, pp. 1083-1097.
Aggarwal et al. "Abdominal aortic aneurysm: A comprehensive review," Experimental and Clinical Cardiology, 2011, pp. 11-15, vol. 16, No. 1, Pulsus Group Inc., London, United Kingdom.
Helgadottir et al., "The same sequence variant on 9p21 associates with myocardial infarction, abdominal aortic aneurysm and intracranial aneurysm", Nature Genet, Feb. 1, 2008, pp. 217-224, vol. 40 | No. 2, Nature Publishing Group, London, United Kingdom.
Holdt et al., "Recent Studies of the Human Chromosome 9p21 Locus, Which Is Associated With Atherosclerosis in Human Populations", Arterioscler Thromb Vasc Bioi., Jan. 18, 2012, pp. 196-206, vo I . 32, No. 2, American Heart Association, Inc., Dallas, TX.
Macsweeney et al. "Pathogenesis of abdominal aortic aneurysm, " British Journal of Surgery, Jul. 1994, pp. 935-941, vol. 81, No. 7, Wiley, Hoboken, NJ.
Thorp et al., "Mechanisms and consequences of efferocytosis in advanced atherosclerosis", Journal of Leukocyte Biology, Nov. 2009, pp. 1089-1095, vol. 86, No. 5, Wiley, Hoblken, NJ.
Toghill et al., "Abdominal aortic aneurysm-an independent disease to atherosclerosis?", Cardiovascular Pathology, Jan. 29, 2017, pp. 71-75, vol. 27, Elsevier, New York City, NY.
Wei et al., "Association of polymorphisms on chromosome 9p21.3 region with increased susceptibility of abdominal aortic aneurysm in a Chinese Han population", Journal of Vascular Surgery, Apr. 2014, pp. 879-885, vol. 59, Issue 4, Elsevier, New York City, NY.
Kurosawa et al. (2013) Current status of medical treatment for abdominal aortic aneurysm. *Circulation Journal*, 77(12), pp. 2860-2866.

* cited by examiner

SEQUENCE LISTING

```
<160> NUMBER OF SEQ ID NOS: 2

<210> SEQ ID NO 1
<211> LENGTH: 118
<212> TYPE: PRT
<213> ORGANISM: Homo sapiens

<400> SEQUENCE: 1

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 2
<211> LENGTH: 119
<212> TYPE: PRT
<213> ORGANISM: Homo sapiens

<400> SEQUENCE: 2

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80
```

-continued

```
Ile Thr Pro Ala Asp Ala Gly Thr Tyr Tyr Cys Ile Lys Phe Arg Lys
             85              90                  95

Gly Ser Pro Asp Asp Val Glu Phe Lys Ser Gly Ala Gly Thr Glu Leu
            100             105             110

Ser Val Arg Ala Lys Pro Ser
        115
```

TARGETING ANEURYSM DISEASE BY MODULATING PHAGOCYTOSIS PATHWAYS

CROSS REFERENCE

This application is a Continuation and claims benefit of 371 application Ser. No. 15/510,591, filed Mar. 10, 2017, which claims benefit of PCT Application No. PCT/US2015/049150, filed Sep. 9, 2015, which claims benefit of U.S. Provisional Patent Application No. 62/050,664, filed Sep. 15, 2014, which applications are incorporated herein by reference in their entirety.

FEDERALLY SPONSORED RESEARCH AND DEVELOPMENT

This invention was made with Government support under contract HL103605 awarded by the National Institutes of Health. The Government has certain rights in the invention.

INCORPORATION BY REFERENCE OF SEQUENCE LISTING PROVIDED AS A TEXT FILE

A Sequence Listing is provided herewith in a text file, STAN-1148CON Seq List_ST25, created on Apr. 4, 2024 and having a size of 2651 bytes. The contents of the text file are incorporated herein by reference in its entirety.

BACKGROUND OF THE INVENTION

Serious vascular defect can result when an area of weakened vessel wall causes a bulge, or bubble, to protrude out in a radial direction from the vessel. Such aneurysms can occur at various positions within the vasculature. Abdominal aortic aneurysms most often develop in the relatively long segment of aorta between the renal arteries and the bifurcation of the aorta into the right and left iliac arteries. Abdominal aortic aneurysms progressively enlarge at variable and unpredictable rates, and as they do, the involved aneurysm wall becomes weaker and thinner, and eventually ruptures. Rupture is relatively uncommon in abdominal aortic aneurysms less than five centimeters maximum transverse diameter, but the risk increases with increasing size. Rupture of abdominal aortic aneurysms has been responsible for approximately 15,000 deaths per year in the United States.

Endovascular repair of aortic aneurysms has been shown to be effective in preventing rupture of abdominal and thoracic aortic aneurysms and has reduced morbidity compared to open surgical repair. Consequently, endovascular repair is now extended to many patients who were not considered to be candidates for aneurysm repair in the past. However, despite the clear benefits of endovascular surgery in the early peri-operative period, there are significant concerns regarding the long-term stability and durability of endovascular repair. Despite these surgical advances, aneurysm disease remains a leading killer and no medical therapies have been convincingly proven to slow aneurysm progression or prevent rupture.

Methods for treating and preventing aneurysm disease are of great interest and are addressed by the present invention.

PUBLICATIONS

Patent publications relating to aortic aneurysms include, inter alia, USRE38146 "Method and apparatus for bilateral intra-aortic bypass"; U.S. Pat. No. 5,578,072, "Aortic graft and apparatus for repairing an abdominal aortic aneurysm"; U.S. Pat. No. 5,522,880, "Method for repairing an abdominal aortic aneurysm"; U.S. Pat. No. 5,489,295, "Endovascular graft having bifurcation and apparatus and method for deploying the same"; U.S. Pat. No. 6,475,466, "Methods for treating endoleaks during endovascular repair of abdominal aortic aneurysms"; U.S. Pat. No. 6,409,756, "Endovascular aortic graft"; U.S. Pat. No. 6,767,359 "Prosthesis for the repair of thoracic or abdominal aortic aneurysms and method therefore"; U.S. Pat. No. 5,643,208, "Balloon device for use in repairing an abdominal aortic aneurysm"; U.S. Pat. No. 4,577,631, "Aneurysm repair apparatus and method"; U.S. Pat. No. 7,112,217, "Biluminal endovascular graft system"; U.S. Pat. No. 7,004,964, "Apparatus and method for deployment of an endoluminal device"; U.S. Pat. No. 6,814,748, "Intraluminal grafting system"; U.S. Pat. No. 6,303,100, "Methods for inhibiting the formation of potential endoleaks associated with endovascular repair of abdominal aortic aneurysms"; U.S. Pat. No. 5,681,346, "Expandable stent forming projecting barbs and method for deploying"; U.S. Pat. No. 5,207,695, "Aortic graft, implantation device, and method for repairing aortic aneurysm"; U.S. Pat. No. 4,313,231, "Vascular prosthesis".

Leeper et al. (2013) Arterioscler Thromb Vasc Biol. 2013; 33:e1-e10, herein specifically incorporated by reference, discusses how loss of CDKN2B promotes p53-dependent smooth muscle cell apoptosis and aneurysm. Co-pending patent application 61/879,562, herein specifically incorporated by reference, discusses the role of modulating efferocytosis in atherosclerotic disease.

SUMMARY OF THE INVENTION

Methods are provided for modulation of efferocytosis/phagocytosis pathways (referred to herein as EP pathways) for treatment and/or prevention of aneurysm disease in a subject. By administering an agent that targets the EP pathway including CDKN2B, calreticulin, and CD47, the EP pathway can be normalized and reduce risk of aneurysm. Aneurysm disease as used herein includes without limitation abdominal aortic aneurysms (AAA disease), thoracic aortic aneurysm, intracranial aneurysms ('berry' aneurysms), post stenotic dilatation, aortic dissection, etc. Abdominal aortic aneurysms are of particular interest.

In some embodiments, the subject is homozygous or heterozygous for a 9p21 risk allele. In some such embodiments the methods include genetic testing of the subject for the presence of a 9p21 risk allele. In other such embodiments the subject has been previously diagnosed for the presence of a 9p21 risk allele. Such diagnostic methods may include, without limitation, analyzing a sample of genomic DNA from the individual for the presence of sequences of human chromosome 9p21 associated risk of CAD, including SNPs associated with the risk locus.

In some embodiments the subject has been diagnosed with an aneurysm, e.g. an aneurysm greater than the normal diameter of the artery. An aortic aneurysm greater than the normal diameter may be, for example greater than about 2 cm diameter of the aorta, and may be less than about the size of an aneurysm for which surgery is indicated, e.g. less than about 6 cm diameter, less than about 5.5 cm diameter, less than about 5 cm diameter. Treatment may be initiated when an aneurysm, including without limitation an aortic aneurysm, is greater than about 2 cm, greater than about 2.5 cm, greater than about 3 cm, greater than about 3.5 cm, greater than about 4 cm, greater than about 4.5 cm, and may be less than about 6 cm, less than about 5.5 cm, less than about 5 cm diameter. The methods of the invention may also include monitoring a known aneurysm through imaging techniques during treatment for changes in size.

In the methods of the invention, an EP agent that increases phagocytosis of components of the diseased blood vessel, including macrophage phagocytosis and efferocytosis of apoptotic smooth muscle cells, is administered to the subject in a dose and for a period of time effective to stabilize, prevent or reduce aneurysm disease in the individual. Molecular targets for increasing efferocytosis and macrophage phagocytosis include, without limitation, agents that activate or increase expression of CDKN2B or Retinoblastoma (Rb), or decrease the expression of E2F4; agents that increase activity or expression of calreticulin; agents that block the interaction of CD47 and SIRPα; and the like. In other embodiments the agent enhances expression of CDKN2B in cardiovascular cells, including, for example, smooth muscle cells. Such agents may include, for example, palbociclib; 5-aza-2'-deoxycytidine in the absence or presence of phenylbutyrate; etc.

In some embodiments, the agent that increases EP pathway activity reduces the interaction of CD47 and SIRPα, which agent may be referred to herein as an anti-CD47 agent. In some embodiments such agents do not interfere with the interaction between CD47 and thrombospondin. Preferred anti-CD47 agents include soluble SIRPα, for example a high affinity soluble SIRPα; anti-CD47 antibodies, anti-SIRPα antibodies, etc.

In some embodiments the EP agent mimics or enhances calreticulin. Calreticulin "mimetics" and "agonists" include molecules that function similarly to, or potentiate, CRT by binding and activating LRP receptor. Molecules useful as CRT mimetics include derivatives, variants, and biologically active fragments of naturally occurring CRT. Molecules useful as agonists include antibodies and other agents that act to enhance the pro-phagocytic activity of CRT.

Another aspect of the present invention relates to the use of an EP stimulating agent in the manufacture of a medicament to stabilize, prevent or reduce aneurysm disease, wherein the medicament is administered to an individual having or at risk of having aneurysm disease.

Still another aspect of the present invention provides a kit to stabilize, prevent or reduce aneurysm disease. The kit includes an phagocytosis stimulating agent, in an amount sufficient to stabilize, prevent or reduce aneurysm disease. The kit may also include reagents for genotyping at human chromosome 9p21, including alleles of rs10757278 and rs1333049. The kit may also instructions for use, reagents for monitoring aneurysm disease, and the like.

DETAILED DESCRIPTION OF THE INVENTION

Figure 1:
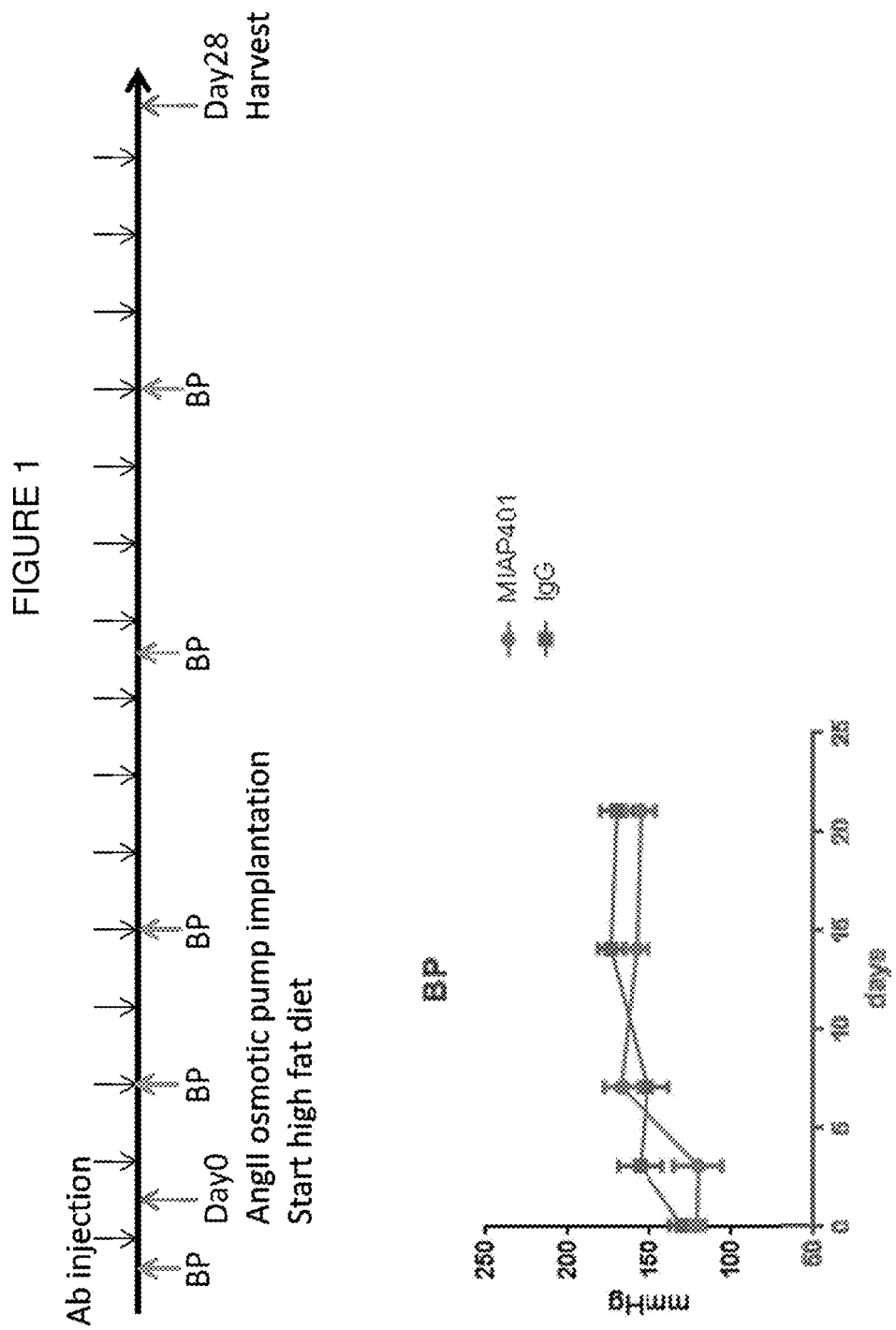
FIG. 1. Overview of atherosclerosis prevention study, showing timeline for anti-Cd47 Ab injection, blood pressure measurement, and high fat diet administration (top). Blood pressure changes over time during the treatment period (bottom).

The present invention relates to methods of treating a subject for aneurysm disease, by administering an agent that increases phagocytosis of diseased vascular tissue, including the efferocytosis and/or phagocytosis of apoptotic smooth muscle cells, which may herein be referred to as an EP agent. In some embodiments, the subject is homozygous or heterozygous for a 9p21 risk allele. In some embodiments, the EP agent provides for one or more of the following activities: reduces the binding of CD47 to SIRPα; increases or mimics the activity of calreticulin, including binding of calreticulin to LRP; or increases expression of CDKN2B.

Aneurysm is a dilation in the wall of an artery, such as the aorta. Aneurysms can develop anywhere along the aorta, including the abdominal aorta and thoracic aorta. Aneurysms can also develop in popliteal arteries, femoral arteries, carotid arteries, cerebral arteries, and coronary arteries. Aneurysms may be saccular or fusiform. Abdominal aortic aneurysms are a major manifestation of atherosclerosis, a disease process that affects the entire vascular system. Thrombus often develop in the aneurysm because blood flow inside the aneurysm is sluggish. The clot may extend along the entire wall of the aneurysm.

The presence of aneurysms can be difficult to diagnose, as many people with aneurysms have no symptoms and are diagnosed by chance when a routine physical examination or an imaging procedure is done. Usually, ultrasonography can clearly show the size of an aneurysm. If an aneurysm is detected, ultrasonography may be repeated every few months to determine if and how quickly the aneurysm is enlarging. Computed tomography (CT) of the abdomen, particularly if done after a radiopaque dye is injected intravenously, can determine the size and shape of an aneurysm more accurately than ultrasonography. Magnetic resonance imaging (MRI) is also accurate.

Aneurysms that are wider than about 5 cm may rupture, and are often treated by inserting a synthetic graft to repair the aneurysm. Typically with endovascular stent grafting a catheter containing the stent-graft is guided over the wire and positioned inside the aneurysm. Then the stent-graft is opened, forming a stable channel for blood flow. If the iliac arteries are involved, the graft must be extended to include them. If the aneurysm extends above the renal arteries, the renal arteries must be reimplanted into the graft, or bypass grafts must be created. Rupture or threatened rupture of an abdominal aortic aneurysm requires emergency open surgery or placement of an endovascular stent-graft. Untreated ruptured abdominal aortic aneurysms are always fatal.

Surgical repair of aneurysms <5 cm does not appear to increase survival, which may in part be due to the complications of surgery. However, such aneurysms should be monitored with ultrasonography every 6 to 12 mo for expansion that warrants treatment. Control of atherosclerotic risk factors is important, and may include treatment by the methods of the invention. If a small or moderate-sized aneurysm becomes >5.5 cm and if risk of perioperative complications is lower than estimated risk of rupture, AAA surgical repair may be indicated.

Surgery typically is performed through an abdominal incision, where the sac of the aneurysm is incised and a synthetic tube is sewn in place to connect the 2 ends of the more normal-sized aorta. Sometimes, the repair has to include one or both of the terminal branches of the aorta (iliac arteries) that may also have become aneurysmal. Bypass of narrowed or blocked aortic branches to the kidneys or abdominal organs may also be required. After the tube is connected at both ends, the wall of the aneurysm is wrapped around the tube. Potential complications from such surgery include bleeding, infection, and kidney or bowel damage. Further, because coronary artery disease is so common among patients with AAA, a major worry is the risk of postoperative heart trouble. As an alternative, a stent draft can be placed through an artery, e.g. femoral artery. The stent covers the entire aneurysm, and the vessel walls eventually shrink around the stent. For example, see Blum et al. (1997) N Engl J Med. 336:13-20.

9p21 Risk. As used herein, the term "an individual carrying at least one 9p21 risk factor" refers to humans in which one or more risk alleles at the 9p21 locus are present in the genome. Such individuals have been shown to have an increased risk of: early onset myocardial infarction, abdominal aortic aneurysm, stroke, peripheral artery disease, and myocardial infarction/coronary heart disease. This risk is independent of traditional risk factors, including diabetes, hypertension, cholesterol, and obesity. See, for example, Helgadottir et al. Science. 2007; 316(5830):1491-1493; Helgadottir et al. Nat Genet. 2008; 40(2):217-224; Palomaki et al. JAMA. 2010; 303(7):648-656; and Roberts et al. Curr Opin Cardiol. 2008; 23:629-633, each herein specifically incorporated by reference.

The 9p21 locus is in tight LD (linkage disequilibrium), and a number of single nucleotide polymorphisms (SNP) markers have been shown to be useful in diagnosis. Representative SNPs include without limitation rs10757278; rs3217992; rs4977574; rs1333049; rs10757274; rs2383206; rs2383207; Rs3217989; rs1333040; rs2383207; rs10116277; rs7044859; rs1292136; rs7865618; rs1333045; rs9632884; rs10757272; rs4977574; rs2891168; rs6475606; rs1333048; rs1333049; Rs1333045; etc.

Efferocytosis and Phagocytosis. The process by which professional and nonprofessional phagocytes dispose of apoptotic cells in a rapid and efficient manner. Efferocytosis involves a number of molecules, including ligands on the apoptotic cells, e.g. phosphatidylserine; receptors on the efferocyte; soluble ligand-receptor bridging molecules; and so-called "find-me" and "don't-eat-me" molecules, e.g., lysophospholipids and CD47, the expression of which by dying cells is altered to attract nearby phagocytes. By clearing apoptotic cells at a relatively early stage of cell death, when the cell plasma and organelle membranes are still intact, postapoptotic, or "secondary", necrosis is prevented. Prevention of cellular necrosis, in turn, prevents the release of potentially damaging intracellular molecules into the extracellular milieu, including molecules that can stimulate inflammatory, proatherosclerotic and/or autoimmune responses.

The efficiency of efferocytic clearance in atherosclerotic lesions plays a key role in disease development. Efferocytosis is known to be impaired in human atherosclerotic plaque. A prominent feature of advanced atherosclerotic lesions is the necrotic core, or lipid core, which is a collection of dead and necrotic macrophages surrounded by inflammatory cells. Necrotic cores are thought to be a major feature responsible for plaque "vulnerability", i.e., plaques capable of undergoing disruption and triggering acute lumenal thrombosis. Plaque disruption and acute thrombosis are the events that trigger acute coronary syndromes, including myocardial infarction, unstable angina, sudden cardiac death, and stroke.

By "manipulating phagocytosis" is meant an up-regulation or a down-regulation in phagocytosis of a targeted cell, e.g. apoptotic SMC, by at least about 10%, or up to 20%, or 50%, or 70% or 80% or up to about 90% compared to level of phagocytosis observed in absence of intervention.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells. However, "non-professional" cells are also known to participate in efferocytosis, such as neighboring SMCs in the blood vessel wall.

"Treatment", "treating", "treat" and the like are used herein to generally refer to obtaining a desired pharmacologic and/or physiologic effect. The effect can be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom. Those in need of treatment include individuals already diagnosed with an aneurysm, as well as those in which the disease is to be prevented.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

An "effective amount" is an amount sufficient to effect beneficial or desired clinical results. An effective amount can be administered in one or more administrations. For purposes of this invention, an effective amount of an EP agent is an amount that is sufficient to palliate, ameliorate, stabilize, reverse, prevent, slow or delay the progression of the disease state, e.g. an aneurysm, by increasing phagocytosis of a target cell.

For example, in an animal model the incidence of death in a sample population due to aneurysm maybe reduced relative to a control treated animal by may be reduced 25%, 50%, 75%. Alternatively, treatment with the methods of the invention may be monitored by reduction or stabilization of an existing aneurysm, for example where the size of an existing aneurysm is stabilized over time relative to an untreated subject, e.g. where an increase is size over time is reduced by up to about 10%, 20%, 30%, 40%, 50%, 60%, 70%, 80%, 90% or more related to an untreated individual. Such monitoring may be performed in a population, e.g. in a clinical trial cohort study.

In some embodiments the subject being treated has been diagnosed with an aneurysm, e.g. an aneurysm greater than the normal diameter of the aorta, which may be, for example greater than about 2 cm diameter, and may be less than about the size of an aneurysm for which surgery is indicated, e.g. less than about 6 cm diameter, less than about 5.5 cm diameter, less than about 5 cm diameter. Treatment may be initiated when an aneurysm, including without limitation an aortic aneurysm, is greater than about 2 cm, greater than about 2.5 cm, greater than about 3 cm, greater than about 3.5 cm, greater than about 4 cm, greater than about 4.5 cm, and may be less than about 6 cm, less than about 5.5 cm, less than about 5 cm diameter.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations. The definition also includes sample that have been enriched for particular types of molecules, e.g., nucleic acids, polypeptides, etc.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides; high affinity binding of a SIRPα polypeptide to CD47; etc.) In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 (i.e., anti-CD47 agents), or that otherwise block the interaction between CD47 and SIRPα, agents that bind to calreticulin or its LRP receptor, etc.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural protein.

A "fusion" polypeptide is a polypeptide comprising a polypeptide or portion (e.g., one or more domains) thereof fused or bonded to heterologous polypeptide. A fusion soluble CRT protein, for example, will share at least one biological property in common with a native sequence soluble CRT polypeptide. Examples of fusion polypeptides include immunoadhesins, as described above, which combine a portion of the polypeptide of interest with an immunoglobulin sequence, and epitope tagged polypeptides, which comprise a soluble polypeptide of interest or portion thereof fused to a "tag polypeptide". The tag polypeptide has enough residues to provide an epitope against which an antibody can be made, yet is short enough such that it does not interfere with biological activity of the polypeptide of interest. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. For example, derivatives and fusion of soluble CRT find use as CRT mimetic molecules.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Cyclin-dependent kinase inhibitor 2B (CDKN2B) is also known as multiple tumor suppressor 2 (MTS-2) or p15INK4B. The Genbank refseq for the human mRNA has the accession number NM_004936 and the protein refseq has the accession number NP_004927. This gene lies adjacent to the tumor suppressor gene CDKN2A in a region that is frequently mutated and deleted in a wide variety of tumors.

CDKN2B forms a complex with CDK4 or CDK6, and prevents the activation of the CDK kinases by cyclin D, thus the encoded protein functions as a cell growth regulator that inhibits cell cycle G1 progression.

It is shown herein that decreased CDKN2B expression associated with 9p21 risk alleles impairs expression of calreticulin, a ligand required for activation of engulfment receptors on phagocytic cells. As a result, cdkn2B-deficient apoptotic bodies, e.g. apoptotic smooth muscle cells, are rendered resistant to efferocytosis and are not efficiently cleared by phagocytic cells. Agents that activate or upregulate CDKN2B expression are known in the art, including, for example, palbociclib (see Toogood et al. (2005) J Med Chem. 48(7):2388-406); 5-aza-2'-deoxycytidine in the absence or presence of phenylbutyrate (see Lemaire et al. (2004) *Leuk Lymphoma.* 45(1):147-54); hypoxia-inducible-factors-1a and -2a (see Aesoey et al. (2013) Endocr Rev, Vol. 34 (03_Meeting Abstracts): SUN-303; etc. Agents that activate or upregulate CDKN2B can be determined by screening methods as known in the art.

Calreticulin. Calreticulin is a multifunctional protein of 417 amino acids, molecular weight 48 kDa, that binds $Ca^{2+}$ ions, rendering it inactive. The $Ca^{2+}$ is bound with low affinity, but high capacity, and can be released on a signal. Calreticulin can be located in storage compartments associated with the endoplasmic reticulum, where it binds to misfolded proteins and prevents them from being exported to the Golgi apparatus. Calreticulin is also found in the nucleus, suggesting that it may have a role in transcription regulation. Calreticulin binds to the synthetic peptide KLGFFKR, which is almost identical to an amino acid sequence in the DNA-binding domain of the superfamily of nuclear receptors. The gene symbol for calreticulin is CALR, and the human sequences may be accessed at Pubmed as follows: Protein Accession #NP_004334; Nucleotide Accession #: NM_004343.

Calreticulin on the surface of apoptotic cells serves as a recognition and clearance ligand by activating the internalization receptor LRP on the responding phagocyte cell surface. The surface expression of calreticulin increases and calreticulin was redistributed during apoptosis, possibly enhancing stimulation of LRP on the phagocyte.

The low density lipoprotein receptor-related protein (LRP) is a 4,544-amino acid protein containing a single transmembrane segment, with a high degree of sequence identity to the LDL receptor. The human genetic sequences may be accessed at Pubmed as follows: Nucleotide Accession #: NM_002332.2 GI:126012561.

Agents that specifically bind to calreticulin (CRT) are of interest as agonists for enhancing the pro-phagocytic activity of CRT. CRT binding agents useful in the methods of the invention include analogs, derivatives and fragments of the original specific binding member, e.g. Fab fragments of antibodies, etc. Calreticulin "mimetics" and "agonists" include molecules that function similarly to or potentiate CRT by binding and activating LRP receptor. Molecules useful as CRT mimetics include derivatives, variants, and biologically active fragments of naturally occurring CRT. Molecules useful as agonists include antibodies and other agents that act to enhance the pro-phagocytic activity of CRT.

Fragments of soluble CRT, particularly biologically active fragments and/or fragments corresponding to functional domains, are of interest. Fragments of interest will typically be at least about 10 aa to at least about 15 aa in length, usually at least about 50 aa in length, but will usually not exceed about 142 aa in length, where the fragment will have a stretch of amino acids that is identical to CRT. A fragment "at least 20 aa in length," for example, is intended to include 20 or more contiguous amino acids from, for example, the polypeptide encoded by a cDNA for CRT. In this context "about" includes the particularly recited value or a value larger or smaller by several (5, 4, 3, 2, or 1) amino acids.

In vitro assays for calreticulin biological activity include, e.g. phagocytosis of porcine cells by human macrophages, binding to LRP, etc. A candidate agent useful as a calreticulin agonist mimetic results in the down regulation of phagocytosis by at least about 10%, at least about 20%, at least about 50%, at least about 70%, at least about 80%, or up to about 90% compared to level of phagocytosis observed in absence of candidate agent.

CD47, also known as integrin associated protein (IAP) is a 50 kDa membrane receptor that has extracellular N-terminal IgV domain, five transmembrane domains, and a short C-terminal intracellular tail transmembrane, belonging to the immunoglobulin superfamily, with interacts with integrins, most commonly integrin $\alpha v\beta 3$, thrombospondin-1 (TSP-1) and signal-regulatory protein alpha (SIRPα). The reference sequence for the human mRNA has the Genbank accession number NM_001025079, and the protein reference sequence is NP_001768.

The CD47/SIRPα interaction leads to bidirectional signaling, resulting in different cell-to-cell responses including inhibition of phagocytosis, stimulation of cell-cell fusion, and T-cell activation.

As used herein, the term "anti-CD47 agent" refers to any agent that reduces the binding of CD47 (e.g., on an affected cell) to SIRPα (e.g., on a phagocytic cell). In some embodiments the anti-CD47 agent does not interfere or bind to the regions of CD47 that bind to thrombospondin. In some embodiments, the anti-CD47 agent does not activate CD47 upon binding. When CD47 is activated, a process akin to apoptosis (i.e., programmed cell death) occurs (Manna and Frazier, Cancer Research, 64, 1026-1036, Feb. 1, 2004). Thus, in some embodiments, the anti-CD47 agent does not directly induce apoptotic cell death of a CD47-expressing cell.

Non-limiting examples of suitable anti-CD47 reagents include a soluble SIRPα polypeptide, which may be a high affinity SIRPa polypeptide, and which is optionally joined to an immunoglobulin domain, e.g. an Fc region, etc., anti-SIRPα antibodies, and anti-CD47 antibodies or antibody fragments. In some embodiments, a suitable anti-CD47 agent (e.g. an anti-CD47 antibody, a high affinity SIRPα reagent, etc.) specifically binds CD47 to reduce the binding of CD47 to SIRPα. In some embodiments, a suitable anti-CD47 agent (e.g., an anti-SIRPα antibody, etc.) specifically binds SIRPα to reduce the binding of CD47 to SIRPα. A suitable anti-CD47 agent that binds SIRPα does not activate SIRPα (e.g., in the SIRPα-expressing phagocytic cell).

The efficacy of a suitable anti-CD47 agent can be assessed by assaying the agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 160%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In one embodiment of the invention, the anti-CD47 agent, or a pharmaceutical composition comprising the agent, is provided in an amount effective to detectably inhibit the binding of CD47 to SIRPα present on the surface of phagocytic cells. The effective amount is determined via empirical testing routine in the art, for example in a biological sample taken from an infected individual. The effective amount may vary depending on the number of cells being targeted, the location of the cells, and factors specific to the subject.

High affinity SIRPα reagent. In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

The high affinity SIRPα reagent of the invention comprises at least one amino acid modification within the d1 domain of SIRPα, which domain is set forth in SEQ ID NO:1, and corresponds to residues 31 to 149 of the native human full-length human protein. The high affinity SIRPα reagent can consist of all or a portion of the d1 domain; and may further comprise one or more amino acids from SIRPα outside of the d1 domain; or may comprise amino acid sequences other than SIRPα, which include without limitation immunoglobulin Fc region sequences.

High affinity SIRPα polypeptides can be at least about 100 amino acids in length, at least about 110, at least about 120, at least about 150, at least about 200 amino acids in length, up to the full-length of the wild-type protein at the transmembrane domain, i.e. about 343 amino acids in length, and is optionally fused to a heterologous polypeptide, e.g. immunoglobulin Fc.

Sets of amino acid changes may include combinations of the above, for example:

V27I or V27L; K53R; S66T or S66G; K68R; and F103V.
L4V or L4I; V27I or V27L; E47V or E47L; K53R; E54Q; S66T or S66G; K68R; V92I; and F103V.
L4V or L4I; V6I or V6L; A21V; V27I or V27L; I31T, I31S or I31F; E47V or E47L; K53R; H56P or H56R; S66T or S66G; K68R; and F94L or F94V.
V6I or V6L; V27I or V27L; I31T, I31S, or I31F; E47V or E47L; K53R; E54Q; H56P or H56R; S66T or S66G; V92I; and F94L or F94V.
L4V or L4I; A21V; V27I or V27L; I31T, I31S, or I31F; E47V or E47L; K53R; E54Q; H56P or H56R; S66G; F94L or F94V; and F103V.
L4V or L4I; V6I or V6L; V27I or V27L; I31T, I31S, or I31F; E47V or E47L; K53R; H56P or H56R; S66T or S66G; K68R; V92I; and F94L or F94V.
L4V or L4I; V6I or V6L; I31T, I31S, or I31F; E47V or E47L; K53R; H56P or H56R; S66T, or S66G; V92I; and F103V.
V6I; V27I; I31F; E47L; K53R; E54Q; H56P; and S66T.
L4V; V6I; V27I; I31F; E47V; K53R; E54Q; H56P; V63I; S66T; K68R; and V92I.
V6I; V27I; I31T; E47V; K53R; E54Q; H56P; S66G; K68R; V92I; and F103V.
V6I; V27I; I31F; E47V; K53R; E54Q; H56P; S66T; and V92I.

In some embodiments, the high affinity SIRPα polypeptide comprises the set of amino acid changes:
{V27I; K53R; S66T; S66G; K68R; F103V};
{L4V; V27L; E47V; K53R; E54Q; S66G; K68R; V92I};
{L4V; V6I; A21V; V27I; I31T; E47L; K53R; H56P; S66T; K68R; F94L};
{V6I; V27I; I31S; I31F; E47V; K53R; E54Q; H56P; S66G; V92I; F94L};
{L4I; A21V; V27I; I31F; E47V; K53R; E54Q; H56P; S66G; F94V; F103V};
{L4V; V6I; V27I; I31F; E47V; K53R; H56R; S66G; K68R; V92I; F94L}; or
{L4V; V6L; I31F; E47V; K53R; H56P; S66G; V92I; F103V}
{V6I; V27I; I31F; E47L; K53R; E54Q; H56P; S66T}
{L4V; V6I; V27I; I31F; E47V; K53R; E54Q; H56P; V63I; S66T; K68R; V92I}
{V6I; V27I; I31T; E47V; K53R; E54Q; H56P; S66G; K68R; V92I; F103V}
{V6I; V27I; I31F; E47V; K53R; E54Q; H56P; S66T; V92I} for example as shown in SEQ ID NO:2.

In some such embodiments, the high affinity SIRPα binding domain is fused or otherwise joined to an immunoglobulin sequence to form a chimeric protein. The immunoglobulin sequence preferably, but not necessarily, is immunoglobulin constant domain(s). The immunoglobulin moiety in such chimeras may be obtained from any species, usually human, and includes IgG1, IgG2, IgG3 or IgG4 subtypes, IgA, IgE, IgD or IgM. The immunoglobulin moiety may comprise one or more domains, e.g. CH1, CH2, CH3, etc.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. In other embodiments, the second polypeptide is any suitable polypeptide that is substantially similar to Fc, e.g., providing increased size, multimerization domains, and/or additional binding or interaction with Ig molecules.

A suitable high affinity SIRPα reagent reduces (e.g., blocks, prevents, etc.) the interaction between the native proteins SIRPα and CD47. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference).

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of infected cells over non-infected cells. Those cells that express higher levels of CD47 (e.g., infected cells) relative to other cells (non-infected cells) will be preferentially phagocytosed. Thus, a suitable anti-SIRPα antibody specifically binds SIRPα without activating/stimulating enough of a signaling response to inhibit phagocytosis.

Suitable antibodies include fully human, humanized or chimeric versions of such antibodies. Humanized antibodies are especially useful for in vivo applications in humans due to their low antigenicity. Similarly caninized, felinized, etc antibodies are especially useful for applications in dogs, cats, and other species respectively.

Methods

Methods are provided for treating or reducing aneurysm disease by administering an agent to an individual that increases efferocytosis and/or phagocytosis of cellular components (EP pathway activity); reducing aneurysm risk or disease. Aneurysm disease may be present in an artery of the individual, including without limitation cerebral arteries, abdominal aorta, thoracic aorta, etc. In some embodiments, the individual is homozygous or heterozygous for a 9p21 risk allele. In some embodiments, the agent that increases activity of the EP pathway provides for one or more of the following activities: reduces the binding of CD47 to SIRPα; increases or mimics the activity of calreticulin, including binding of calreticulin to LRP; or increases expression of CDKN2B. Such methods include administering to a subject in need of treatment a therapeutically effective amount or an effective dose of an EP pathway stimulating agent, including without limitation combinations of the agent with another drug. Methods of administration to the cardiovascular system are of interest, although oral formulations may also find use.

Effective doses of the therapeutic entity of the present invention vary depending upon many different factors, including the nature of the agent, means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage can range from about 0.0001 to 500 mg/kg, and more usually 0.01 to 100 mg/kg, of the host body weight. For example dosages can be 1 mg/kg body weight or 10 mg/kg body weight or within the range of 1-50 mg/kg. The dosage may be adjusted for the molecular weight of the reagent. An exemplary treatment regime entails administration daily, semi-weekly, weekly, once every two weeks, once a month, etc. In another example, treatment can be given as a continuous infusion. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient. It will be understood by one of skill in the art that such guidelines will be adjusted for the molecular weight of the active agent, e.g. in the use of polypeptide fragments, in the use of antibody conjugates, in the use of high affinity SIRPα reagents, etc. The dosage may also be varied for localized administration, e.g. intranasal, inhalation, etc., or for systemic administration, e.g. i.m., i.p., i.v., and the like.

For the treatment of disease, the appropriate dosage of the agent will depend on the severity and course of the disease, whether the agent is administered for preventive purposes, previous therapy, the patient's clinical history and response to the antibody, and the discretion of the attending physician.

The agent is suitably administered to the patient at one time or over a series of treatments.

Suitable agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an efferocytosis stimulating agent includes use in combination with another therapeutic agent, e.g., drugs useful in the treatment of atherosclerosis. Such combinations may include, without limitation, statins. Statins are inhibitors of HMG-COA reductase enzyme. These agents are described in detail; for example, mevastatin and related compounds as disclosed in U.S. Pat. No. 3,983,140; lovastatin (mevinolin) and related compounds as disclosed in U.S. Pat. No. 4,231,938; pravastatin and related compounds as disclosed in U.S. Pat. No. 4,346,227; simvastatin and related compounds as disclosed in U.S. Pat. Nos. 4,448,784 and 4,450,171; fluvastatin and related compounds as disclosed in U.S. Pat. No. 5,354,772; atorvastatin and related compounds as disclosed in U.S. Pat. Nos. 4,681,893, 5,273,995 and 5,969,156; and cerivastatin and related compounds as disclosed in U.S. Pat. Nos. 5,006,530 and 5,177,080. Additional agents and compounds are disclosed in U.S. Pat. Nos. 5,208,258, 5,130,306, 5,116,870, 5,049,696, RE 36,481, and RE 36,520. Statins include the salts and/or ester thereof.

Other drugs useful in combination include, for example, fibrates such as gemfibrozil, fenofibrate, etc.; niacin; zetia; bile acid sequestrants, e.g. cholestyramine, colestipol, colesevelam; lovaza, vascepa; drugs to reduce hypertension, etc.

Therapeutic formulations comprising one or more agents of the invention are prepared for storage by mixing the agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the agent to be administered will be governed by such considerations, and is the minimum amount necessary to treat or prevent atherosclerosis.

The agent can be administered by any suitable means, including topical, oral, parenteral, subcutaneous, intraperitoneal, intrapulmonary, and intranasal. Parenteral infusions include intramuscular, intravenous, intraarterial, intraperitoneal, intrathecal or subcutaneous administration. In addition, the agent can be suitably administered by pulse infusion, particularly with declining doses of the agent.

The agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™ agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent by non-covalent associations, such as non-covalent bonding or by encapsulation. The nature of the carrier can be either soluble or insoluble for purposes of the invention. Those skilled in the art will know of other suitable carriers for binding anti-CD47 agents, or will be able to ascertain such, using routine experimentation.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent through an acceptable chemical linker or chelation carrier. Positron emitting moieties for use in the present invention include $^{18}F$, which can be easily conjugated by a fluorination reaction with the agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Genetic Screening

In one aspect of the present invention, an individual is tested for the presence of a 9p21 risk allele prior to treatment. Such methods comprise an analysis of genomic DNA in an individual for a 9p21 allele that confers an increased susceptibility to atherosclerosis and aneurysm disease. Individuals are screened by analyzing their genomic sequence at 9p21, e.g. rs10757278 or rs1333049 or another representative 9p21 SNP sequences for the presence of a predisposing allele, as compared to a normal sequence.

A number of methods are used for determining the presence of a predisposing variant in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about $10^5$ cells. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki et al. (1985) Science 239:487, and a review of current techniques may be found in McPherson et al. (2000) PCR (Basics: From Background to Bench) Springer Verlag; ISBN: 0387916008. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Primer pairs are selected from the genomic sequence using conventional criteria for selection. The primers in a pair will hybridize to opposite strands, and will collectively flank the region of interest. The primers will hybridize to the complementary sequence under stringent conditions, and will generally be at least about 16 nt in length, and may be 20, 25 or 30 nucleotides in length. The primers will be selected to amplify the specific region suspected of containing the predisposing mutation. Typically the length of the amplified fragment will be selected so as to allow discrimination between repeats of 3 to 7 units. Multiplex amplification may be performed in which several sets of primers are combined in the same reaction tube, in order to analyze multiple exons simultaneously. Each primer may be conjugated to a different label.

The exact composition of the primer sequences are not critical to the invention, but they must hybridize to the flanking sequences under stringent conditions. Criteria for selection of amplification primers are as previously discussed. To maximize the resolution of size differences at the locus, it is preferable to choose a primer sequence that is close to the SNP sequence, such that the total amplification product is at least about 30, more usually at least about 50, preferably at least about 100 or 200 nucleotides in length, which will vary with the number of repeats that are present, to not more than about 500 nucleotides in length. The number of repeats has been found to be polymorphic, as previously described, thereby generating individual differences in the length of DNA that lies between the amplification primers. Conveniently, a detectable label is included in the amplification reaction. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products can be size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59-74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98-111. The size of the amplification product is proportional to the number of repeats (n) that are present at the locus specified by the primers. The size will be polymorphic in the population, and is therefore an allelic marker for that locus. The amplified or cloned fragment is alternatively sequenced by various high methods known in the art.

The presence of a predisposing risk allele is indicative that an individual is at increased risk of developing atherosclerosis and may benefit from treatment by the methods of the invention, although the methods can additionally find use in individuals without a 9p21 genetic risk factor. The diagnosis of a disease predisposition allows the affected individual to seek early treatment of potential lesions, and to avoid activities that increase risk for cardiovascular disease.

Drug Screening

Screening assays identify compounds that modulate the expression or activity of proteins involved in the EP pathway, including without limitation CDKN2B, calreticulin, CD47, SIRPα, etc. An EP pathway stimulating agent can act as the basis for amelioration of aneurysm, particularly abdominal aortic aneurysm. Such compounds may include, but are not limited to peptides, antibodies, or small organic or inorganic compounds. Methods for the identification of such compounds are described below.

Cell- and animal-based systems can act as models for cardiovascular disease and are useful in such drug screening. The animal- and cell-based models may be used to identify drugs, pharmaceuticals, therapies and interventions that are effective in treating cardiovascular disease. In addition, such animal models may be used to determine the $LD_{50}$ and the $ED_{50}$ in animal subjects, and such data can be used to determine the in vivo efficacy of potential cardiovascular disease treatments. Animal-based model systems of cardiovascular disease may include, but are not limited to, non-recombinant and engineered transgenic animals. Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty, for example. Additionally, animal models exhibiting cardiovascular disease symptoms may be engineered by utilizing, for example, smooth muscle cell marking, knockouts of CDKN2B, etc. gene sequences in conjunction with techniques for producing transgenic animals that are well known to those of skill in the art. For example, target gene sequences may be introduced into, and knocked out or overexpressed in the genome of the animal of interest. Animals of any species, including, but not limited to, mice, rats, rabbits, guinea pigs, pigs, micro-pigs, goats, and non-human primates, e.g., baboons, monkeys, and chimpanzees may be used to generate cardiovascular disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313-321); electroporation of embryos (Lo, 1983, Mol Cell. Biol. 3:1803-1814); and sperm-mediated gene transfer (Lavitrano et al., 1989, Cell 57:717-723); etc.

Specific cell types within the animals may be analyzed and assayed for cellular phenotypes characteristic of cardiovascular disease. In the case of monocytes, such phenotypes may include but are not limited to increases in rates of LDL uptake, adhesion to endothelial cells, transmigration, foam cell formation, fatty streak formation, and production of foam cell specific products. Further, such cellular phenotypes may include a particular cell type's fingerprint pattern of expression as compared to known fingerprint expression profiles of the particular cell type in animals exhibiting cardiovascular disease symptoms. The ability of smooth muscle cells to be taken up by phagocytes is of particular interest.

Cells that are down-regulated in CDKN2B activity can be utilized to identify compounds that exhibit anti-cardiovascular disease activity. In the case of monocytes, such phenotypes may include but are not limited to increases in rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ and GM-CSF. Transmigration rates, for example, may be measured using an in vitro system to quantify the number of monocytes that migrate across the endothelial monolayer and into the collagen layer of the subendothelial space.

In vitro systems may be designed to identify compounds capable of activating efferocytosis. Such compounds may include, but are not limited to, peptides made of D- and/or L-configuration amino acids, phosphopeptides, antibodies, and small organic or inorganic molecules. The principle of the assays used to identify compounds that upregulate CDKN2B or calreticulin involves preparing a reaction mixture of the protein and a test compound under conditions and for a time sufficient to allow the two components to interact, and detecting the resulting change in the desired biological activity. Alternatively, a simple binding assay can be used as an initial screening method. These assays can be conducted in a variety of ways. For example, one method to conduct such an assay would involve anchoring a protein or a test substance onto a solid phase and detecting complexes anchored on the solid phase at the end of the reaction.

In a binding assay, the reaction can be performed on a solid phase or in liquid phase. In a solid phase assay, the nonimmobilized component is added to the coated surface containing the anchored component. After the reaction is complete, unreacted components are removed under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a binding reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Cell-based systems such as those described above may be used to identify compounds that act to ameliorate cardiovascular disease symptoms. For example, such cell systems may be exposed to a test compound at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype.

In addition, animal-based disease systems, such as those described, above may be used to identify compounds capable of ameliorating disease symptoms. Such animal models may be used as test substrates for the identification of drugs, pharmaceuticals, therapies, and interventions, which may be effective in treating disease. For example, animal models may be exposed to a compound, suspected of exhibiting an ability to ameliorate cardiovascular disease symptoms, at a sufficient concentration and for a time sufficient to elicit such an amelioration of disease symptoms in the exposed animals. The response of the animals to the exposure may be monitored by assessing the reversal of disorders associated with disease, for example, by counting the number of atherosclerotic plaques and/or measuring their size before and after treatment.

With regard to intervention, any treatments that reverse any aspect of cardiovascular disease symptoms should be considered as candidates for human disease therapeutic intervention. Dosages of test agents may be determined by deriving dose-response curves.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Mice. Male apoE$^{-/-}$ mice (backcrossed onto a C57BL/6 background) were bred by our laboratory as previously described and housed in a specific, pathogen-free environment. Standard sterilized laboratory diet and water were available ad libitum. At Day 0 the animals were initiated on a high fat Western diet (21% anhydrous milk fat, 19% casein and 0.15% cholesterol, Dyets no. 101511) for the ensuing weeks.

AngII Infusion. Mice (8 to 10 weeks old) were implanted with minipumps that delivered AngII subcutaneously at a dose of 1000 ng/kg$^{-1}$/min$^{-1}$, as described previously (see Daugherty et al. (1999) Ann N Y Acad Sci. 892: 108-118.

Antibodies. Rat IgG2a monoclonal antibody miap301 (see Jiang et al. (1999) J Biol Chem. 274(2):559-62) reacts with mouse CD47. Normal rat IgG was used as a control. The antibody was injected into the animals at 200 μg/day i.p. with the schedule shown in FIG. 1.

Tissue. Anesthetized mice were cut open ventrally. Left cardiac ventricles were perfused with phosphate-buffered saline (20 mL) under physiologic pressure with an exit through the severed right atria. Suprarenal regions of abdominal aorta were identified between the last pair of intercostal arteries and the right renal branch. The mesenteric and renal branches and the aorta distal to the right renal branch were ligated with silk sutures, and the suprarenal aorta was harvested. This portion of aorta, measuring ≈5 mm in length, was infused with ≈0.3 mL of OCT compound with a 21-gauge needle to attain full distension. Thoracic aortas between the left subclavian artery and the last pair of intercostal arteries were also harvested. The orientation of aortas was noted, and tissues were frozen immediately.

Pathology and Immunocytochemistry. Aortas were obtained at selected intervals after the initiation of AngII infusions and antibody treatment, and were sectioned longitudinally or by cross sections (7 µm thick). For characterization of cross sections, aortic sections were collected serially from the proximal to the distal aorta. Histology was determined in sections that were taken at intervals of 200 µm. For longitudinal examination of tissues, 7-µm sections were also placed at 200-µm intervals on slides. Standard histologic staining was performed.

Immunocytochemical staining was performed to identify macrophages (MAC3) and smooth muscle (anti-smooth muscle actin (α-SMA)). At least 2 slides, containing ≈15 tissue sections, from each animal were examined for each cell type. A peroxidase-based ABC system and the red chromogen AEC were used to detect the antigen-antibody reaction. Controls included isotype-matched antibodies and nonimmune sera.

Results

At day 30 the mortality for the control IgG group was 25%, 3 out of 12. All had an aortic dissection. The anti-CD47 treated group had a mortality rate of 16.6% (2 out of 12), and one animal had an aortic dissection.

Figure 2:
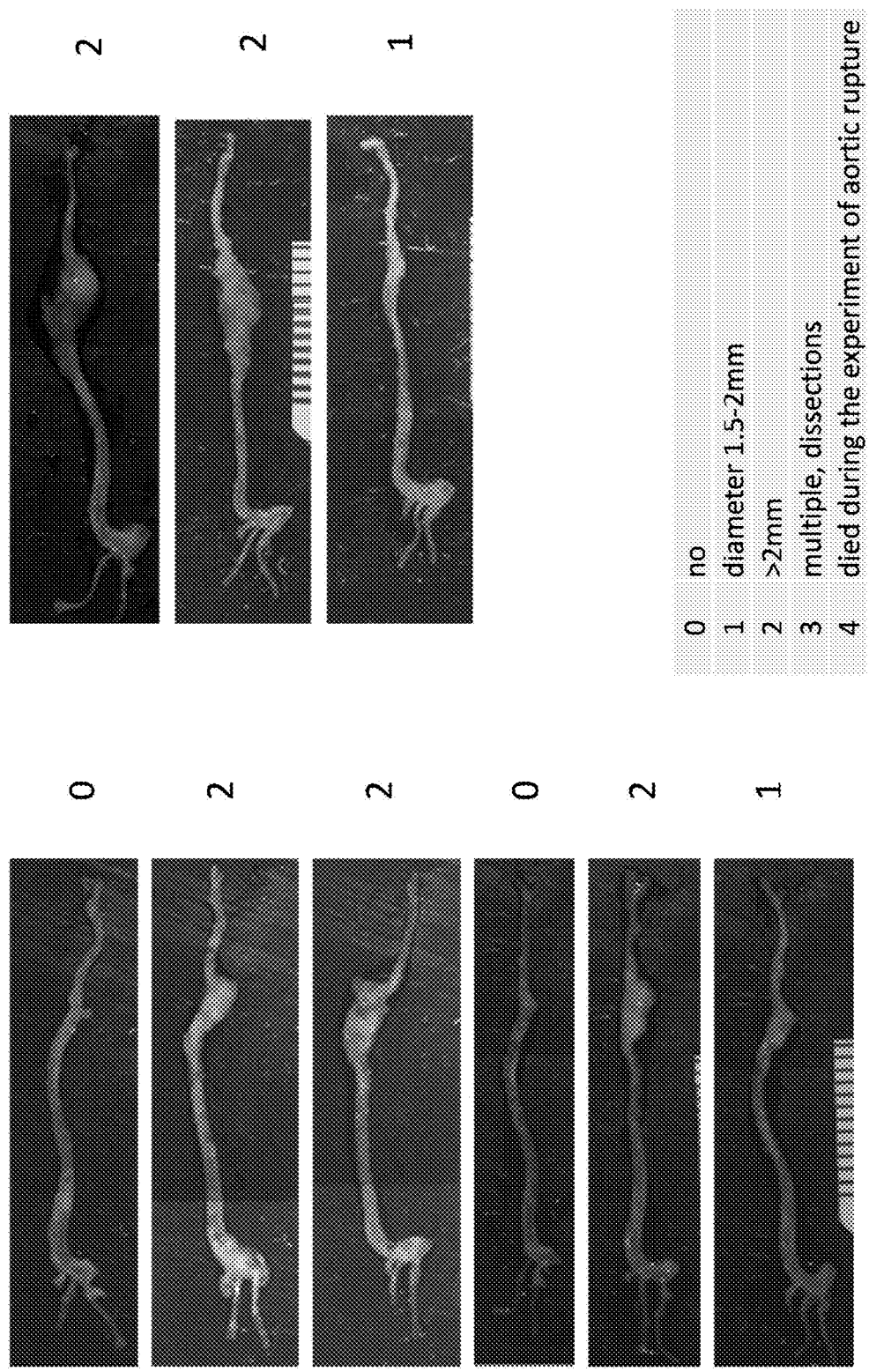
FIG. 2. Representative explanted aortas from control Ab treated mice (IgG) reveal a high incidence of aneurysms after angiotensin infusion. Inset reveals aneurysm scoring system (0-4, with 0 having no aneurysm, and 4 representing a mouse which died of aortic rupture during the treatment period).
Figure 3:
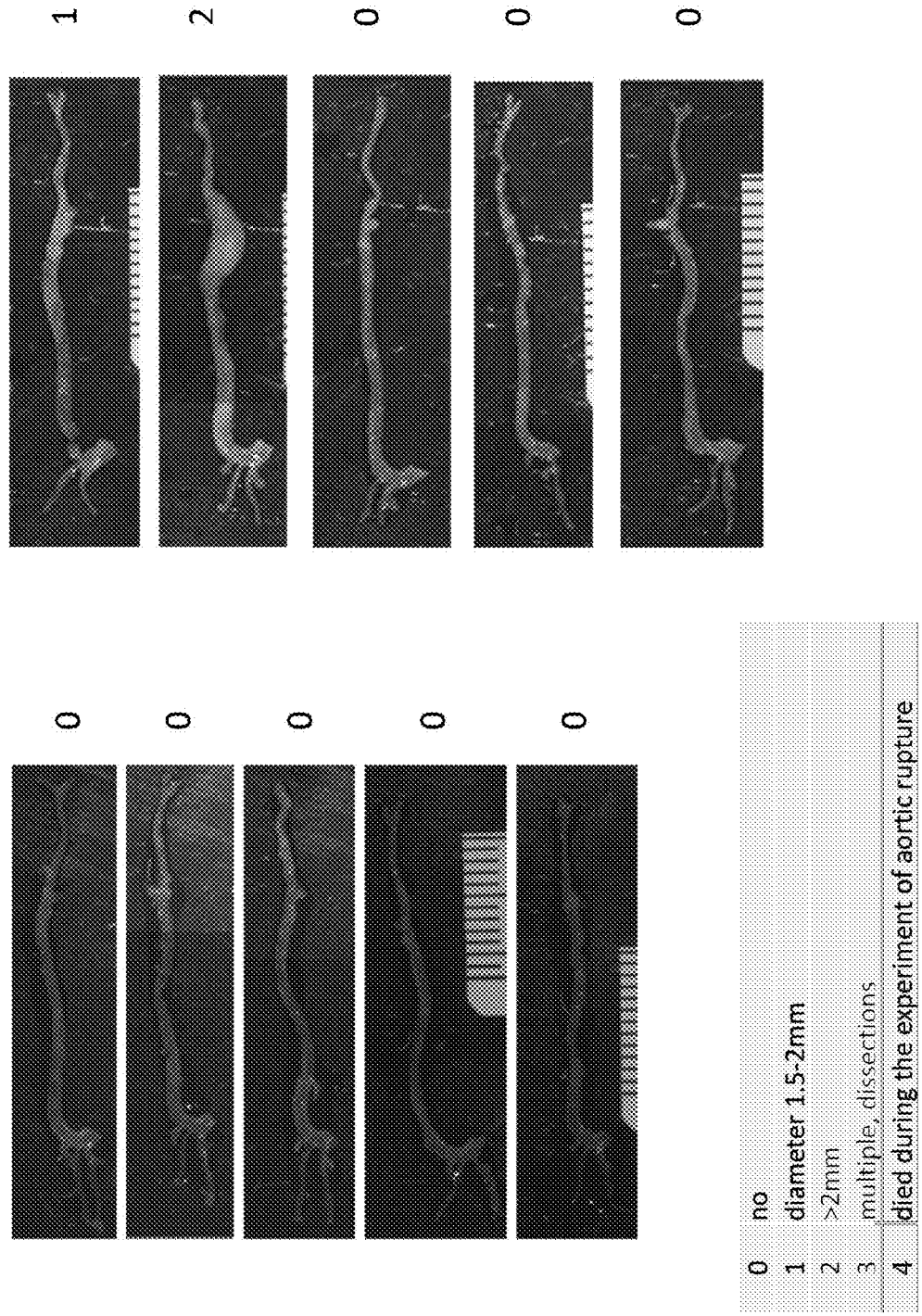
FIG. 3. Representative explanted aortas from antiCD47 Ab treated mice (MIAP410) reveal a low incidence of aneurysms after angiotensin infusion. Inset reveals aneurysm scoring system (0-4, with 0 having no aneurysm, and 4 representing a mouse which died of aortic rupture during the treatment period).
Figure 4:
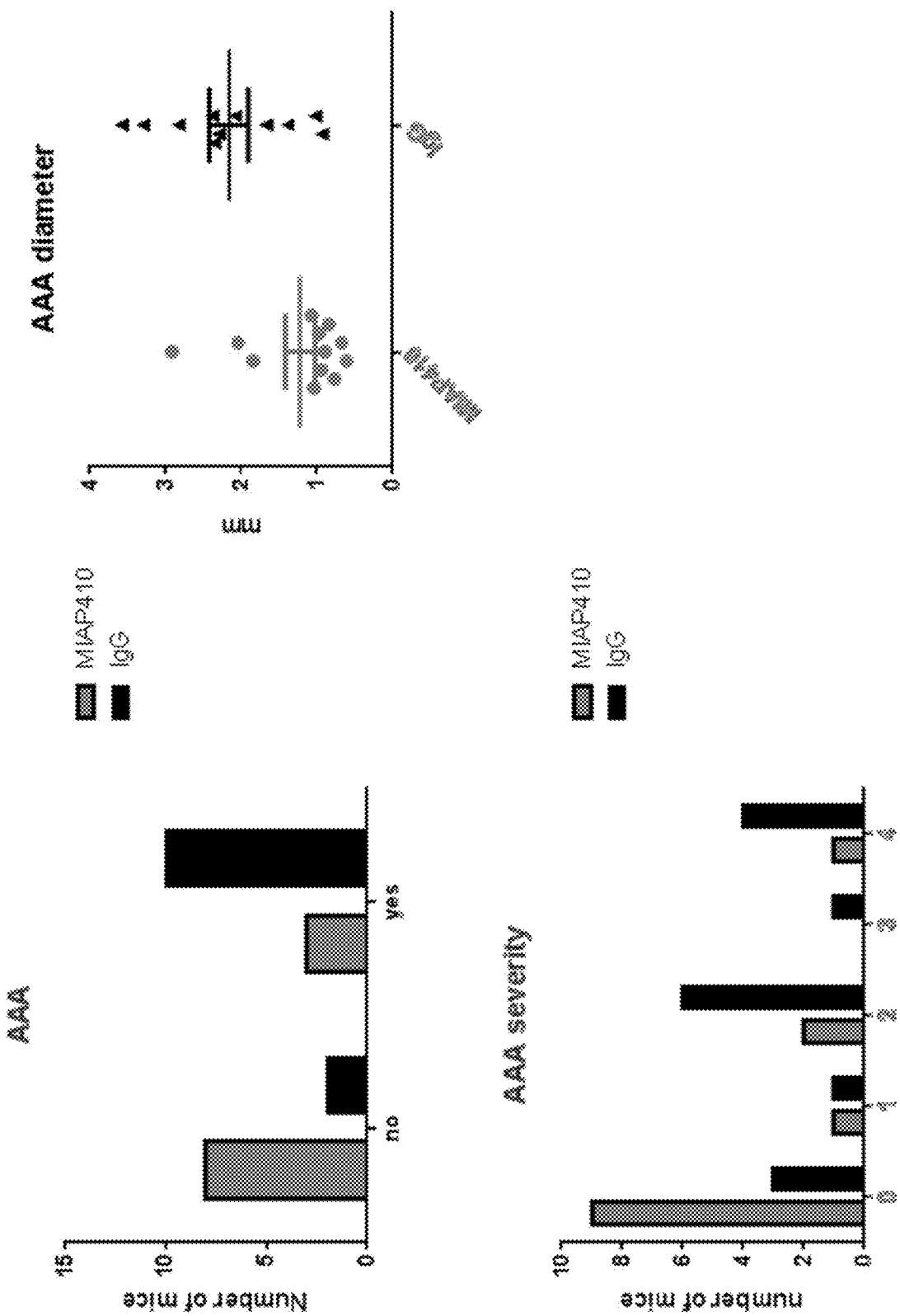
FIG. 4. Comparison of control Ab (IgG) and antiCD47 Ab (MIAP410) treated mice reveals that antiCD47 Ab treatment prevents aneurysm development (Top Left), reduces aneurysm size (Top Right) and reduces aneurysm severity (Bottom, scale as in preceding panels). All differences significant with p value<0.01.

The dissected aorta of the test animals from the control group (FIG. 2) and the anti-CD47 treated group (FIG. 3) show the differences in aneurysm size and severity, which data is summarized in FIG. 4.

What is claimed:

1. A method of treating a subject for aneurysm disease, the method comprising:

administering to a subject that has been diagnosed with an aortic aneurysm, an effective dose a high affinity signal regulatory protein α (SIRPα) reagent that specifically binds to CD47 and reduces the binding of CD47 on an apoptotic cell to SIRPα on a phagocytic cell and thereby increases an efferocytosis and/or phagocytosis of components of a diseased vessel wall; wherein the high affinity SIRPα reagent is a polypeptide variant of wild-type human SIRPα, wherein the polypeptide variant lacks an SIRPα transmembrane domain and comprises a d1 domain of human SIRPα comprising at least one amino acid change relative to the wild-type human SIRPα sequence, wherein the amino acid change increases the affinity of the SIRPα polypeptide to CD47, and wherein the polypeptide variant is fused to an immunoglobulin Fc sequence, thereby reducing or inhibiting symptoms of aneurysm.

2. The method of claim 1, wherein the subject is a human.

3. The method of claim 1, wherein the aneurysm is from 2 to 6 cm diameter.

4. The method of claim 1, wherein the SIRPα variant is a dimer multimerized by the Fc sequence.

5. The method of claim 1, wherein the immunoglobulin Fc sequence is an IgG4 Fc sequence.

6. The method of claim 5, wherein the polypeptide variant comprises V6I, V27I, I31F, E47V, K53R, E54Q, H56P, S66T, and V92I, where the numbering is made relative to SEQ ID NO:1.

7. The method of claim 1, wherein the at least one amino acid change relative to the wild-type SIRPα sequence is selected from V6I, V27I, I31F, E47V, K53R, E54Q, H56P, S66T, V92I, and a combination thereof, where the numbering is made relative to SEQ ID NO:1.

* * * * *

UNITED STATES PATENT AND TRADEMARK OFFICE
CERTIFICATE OF CORRECTION

| | | |
|---|---|---|
| PATENT NO. | : 12,091,456 B2 | Page 1 of 1 |
| APPLICATION NO. | : 17/029814 | |
| DATED | : September 17, 2024 | |
| INVENTOR(S) | : Nicholas J. Leeper et al. | |

It is certified that error appears in the above-identified patent and that said Letters Patent is hereby corrected as shown below:

In the Claims

Column 25, Claim 1, Line 17 should read:
aortic aneurysm, an effective dose of a high affinity signal Signed and Sealed this
Twenty-sixth Day of November, 2024

Katherine Kelly Vidal
*Director of the United States Patent and Trademark Office*